United States Patent [19]
Hutchings

[11] Patent Number: 5,091,107
[45] Date of Patent: Feb. 25, 1992

[54] CHLORINE DIOXIDE GENERATING DEVICE

[75] Inventor: Richard S. Hutchings, Cincinnati, Ohio

[73] Assignee: The Drackett Company, Cincinnati, Ohio

[21] Appl. No.: 424,844

[22] Filed: Oct. 20, 1989

[51] Int. Cl.$^5$ .............................. C01B 11/24
[52] U.S. Cl. .................. 252/187.21; 252/187.23; 422/37; 604/305; 222/187; 118/268
[58] Field of Search ............. 252/187.21, 187.23; 222/187; 118/268; 422/29, 37; 604/305

[56] References Cited

U.S. PATENT DOCUMENTS

| | | | |
|---|---|---|---|
| 4,247,531 | 1/1987 | Hicks | 252/187.21 |
| 4,259,383 | 3/1981 | Eggensperger et al. | 422/37 |
| 4,585,482 | 4/1986 | Tice et al. | 252/187.21 |
| 4,689,169 | 8/1987 | Mason et al. | 252/187.23 |
| 4,709,423 | 12/1987 | Richards | 422/37 |
| 4,731,193 | 3/1988 | Mason et al. | 252/187.21 |
| 4,822,512 | 4/1989 | Auchincloss | 252/187.21 |
| 4,969,880 | 11/1990 | Zamierowski | 604/305 |
| 4,990,334 | 2/1991 | Longino et al. | 252/187.26 |

Primary Examiner—Robert L. Stoll
Assistant Examiner—Joseph D. Anthony
Attorney, Agent, or Firm—Charles J. Zeller

[57] ABSTRACT

The present invention relates to methods and devices for the production of controlled quantities of chlorine dioxide at concentrations which are effective to function as a deodorant or a germicide. Aqueous chlorite compositions such as aqueous sodium chlorite are brought into contact at a controlled rate through capillary means, e.g. a wick with an absorbent pad containing acid or other reactant which will react with the chlorite and from chlorine dioxide.

5 Claims, 3 Drawing Sheets

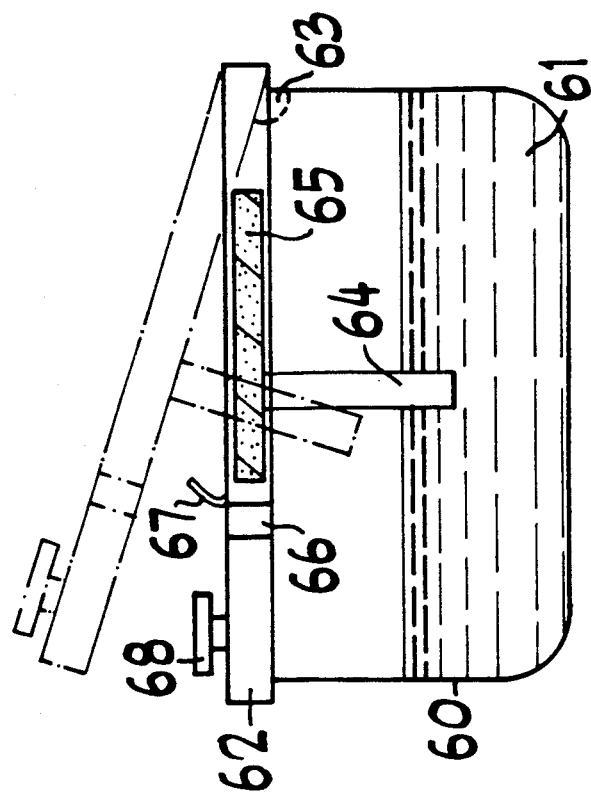
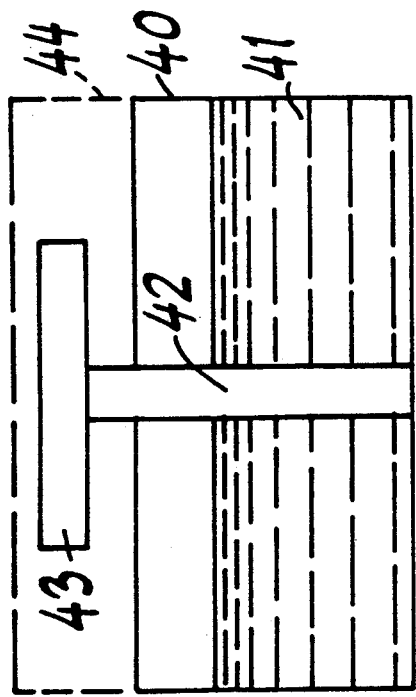
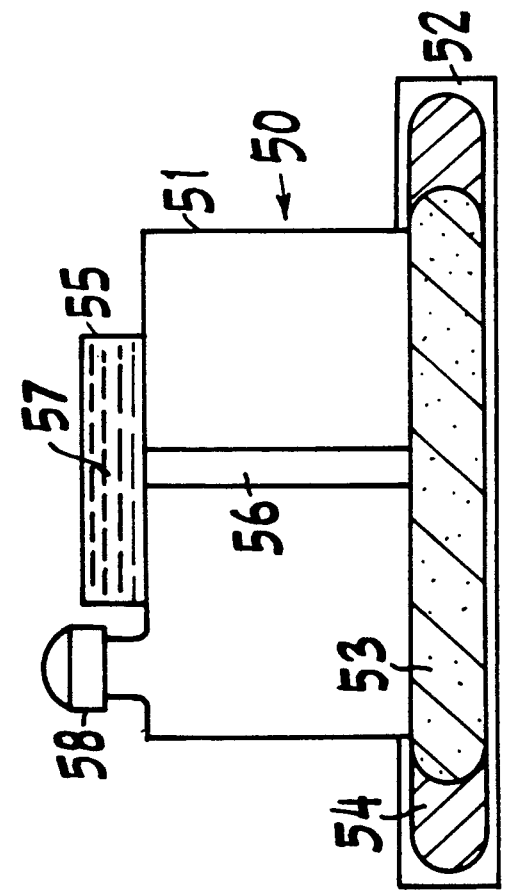

CHLORINE DIOXIDE GENERATING DEVICE

FIELD OF THE INVENTION

The present invention relates to methods for the continuous production of chlorine dioxide at concentration levels sufficient to eliminate odors and act as a germicide. It relates also to compositions useful for achieving such levels of chlorine dioxide gas and to devices for reacting the compositions at a controlled rate to achieve the desired concentration for deodorant or germicidal activity.

BACKGROUND OF THE INVENTION

Chlorine dioxide is known for its deodorizing ability whereby odoriferous chemicals are oxidized to compounds which have essentially no odor. Such compounds include, for example, aldehydes, amines and thiols which are oxidized respectively to alcohols or acids, nitro compounds or various intermediates such as nitroso compounds, and to disulfides or oxides of sulfur.

U.S. Pat. No. 4,104,190 to Hartshorn discloses a solid composition capable of generating chlorine dioxide when dissolved in water, the solid composition containing sodium chlorite and a chlorine release agent. When dissolved in water, the chlorine species provided by the chlorine release agent reacts with the chlorite to form chlorine dioxide. Suitable chlorine release agents include sodium N-chloro-p-toluene-sulfonamide, and sodium dichloroisocyanurate. In an alternate embodiment, a chlorite-free solid composition containing the chlorine release agent may be added to an aqueous solution of stabilized sodium chlorite, as disclosed in U.S. Pat. No. 3,123,521 to Wentworth, et al. In a preferred embodiment, the solid composition also contains an effervescent agent.

Recently, U.S. Pat. No. 4,084,747 to Alliger (U.S. Pat. No. Re. 31,779) proposed the incorporation of lactic acid in an aqueous sodium chlorite composition, the lactic acid lowering the pH of the aqueous media to less than about 7, thereby promoting the formation of chlorine dioxide. The patent states that it is preferable to form the composition by admixture of a sodium chlorite-containing portion and a lactic acid-containing portion within 48 hours of use, for optimum germ-killing effect. To this end, U.S. Pat. No. 4,330,531, also to Alliger, discloses applicators whereby the chlorite portion and the lactic acid portion may be admixed at the time of use. The '531 patent discloses compositions for acne treatment, soaps, and toothpaste.

Another two-part composition is disclosed in Mason, et al., U.S. Pat. No. 4,731,193, which comprises a first part containing stated concentrations of dodecylbenzene sulfonic acid, a phosphate ester, hexamethylene glycol, hydrochloric acid, sodium xylene sulfonate, and water, and a second part containing an aqueous solution of sodium chlorite and sodium xylene sulfonate. The first and second parts are diluted with water.

Kenjo, et al., U.S. Pat. No. 4,731,192, discloses a two-composition cleaning system for contact lenses wherein free oxygen is released when a composition containing a chlorite salt, in aqueous solution, and a solid composition containing solid acid or organic acid salt, an oxygen-consuming agent, and polyvinyl pyrrolidone are combined. Reducing sugars may be included with the solid composition part. Suitable solid acids are tartaric, citric, lactic, malic and gluconic acids.

Chlorine dioxide when released may be employed as a deodorant and, if released in sufficiently high quantities and under carefully controlled conditions as an agent for killing bacteria and other infectious agents.

Chlorine dioxide is extremely effective as an odor eliminator even at concentrations in air as low as 0.01 ppm or lower. At concentrations appreciably above this level it is offensive to the olefactory system and, at sufficiently high concentrations, toxic.

It is a principal object of this invention, therefore, to produce chlorine dioxide at levels which are sufficiently high to eliminate odors but not sufficiently high to be toxic.

It is a further object of this invention to produce chlorine dioxide at levels which are sufficiently high to be germicidally effective.

It is a further object of the invention to produce such levels of chlorine dioxide in a controlled manner so that the continuity of production can be interrupted when desired and continuous production thereafter resumed.

A still further object of the invention is to provide compositions and devices for achieving the foregoing objects.

In practice, the inventions described and claimed herein when utilized for reducing odors, will be employed to eliminate a variety of odors such as pet odors and trash can odors. They are particularly useful when employed as room deodorants especially for the elimination of smoke odors from the atmosphere and from soft surfaces including fabrics such as the fabrics in upholstery, carpets, curtains and drapes.

SUMMARY OF THE INVENTION

The invention provides a method for the continuous production of controlled quantities of chlorine dioxide in which an aqueous solution of an alkali metal chlorite such as sodium chlorite is delivered at a selected rate and concentration from a first absorbent carrier to a second absorbent carrier containing an acid or other chemical reagent which will react with the chlorite to produce chlorine dioxide. A molar excess of acid or other reactant is employed to insure maximum production of chlorine dioxide. The chlorine dioxide is released to the atmosphere along with water vapor by evaporation. Since chlorine dioxide is a water soluble gas it may be advantageous to incorporate in the aqueous solution another chemical which will react with the acid to form carbon dioxide. The carbon dioxide will assist in expelling or purging the chlorine dioxide from the water.

In one preferred embodiment, the aqueous sodium chlorite composition is contained in a reservoir closed with a closure containing an absorbent wick through which the aqueous composition rises by capillary action. The end of the wick remote from the reservoir is in contact with an absorbent emanator pad containing the reactive acid. The first reaction zone for the acid and the chlorite is the point of contact of the wick and the emanator pad. The reaction zone expands radially as the aqueous sodium chlorite continues to rise through the wick and the acid at the reaction interface is consumed.

BRIEF DESCRIPTION OF THE DRAWINGS

FIG. 5 is a cross-sectional view of the fourth embodiments of such devices;

FIG. 6A is a cross-sectional view of the fifth embodiment of such devices;

FIG. 7 is a side-cross-sectional view of the sixth embodiment of the present invention.

DETAILED DESCRIPTION OF THE INVENTION AND PREFERRED EMBODIMENTS

Figure 1:
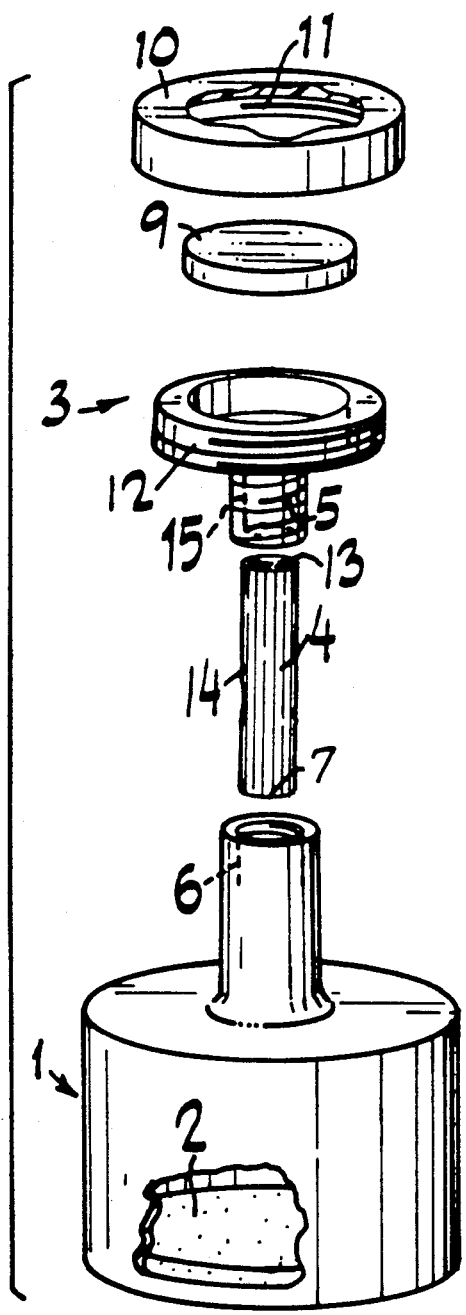
FIG. 1 shows an exploded perspective view of the first embodiment of a device for the delivery of chlorine dioxide in accordance with the invention.
Figure 2:
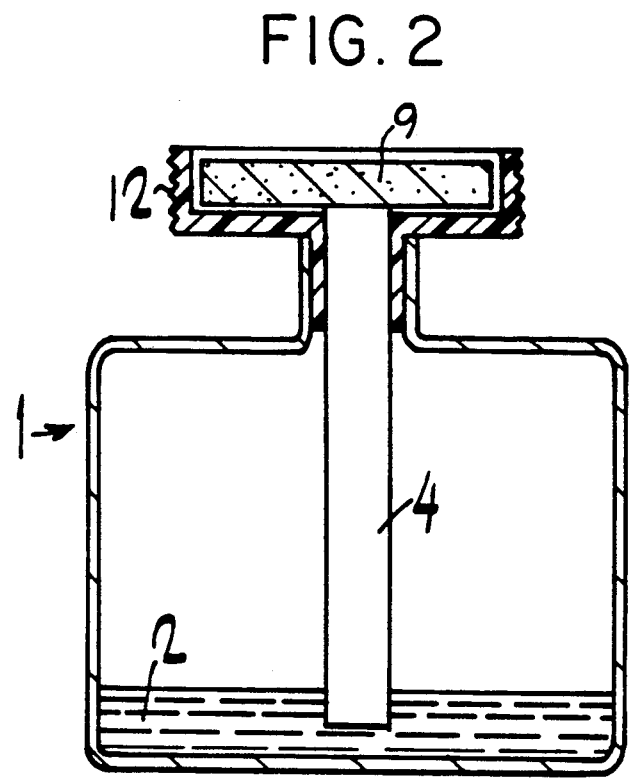
FIG. 2 shows a cross-sectional view of the device of FIG. 1 after it has been assembled.

In the FIGS. 1 and 2 a container generally represented by 1 contains an aqueous sodium chlorite composition 2. The container 1 is provided with an insert member 3 adapted to carry a wick 4. The insert member 3 is constructed with external neck threads 5 so that it can be releasably threaded into the container 2 in mesh with the internal neck container threads 6. The length of the wick 4 is selected so that its end 7 proximate the reservoir 2 can be dipped into the reservoir or removed therefrom by rotating the insert member 3. The insert member 3 includes an upper carrier portion 12 which serves as an emanator pad holder for emanator or absorbent pad 9. A closure member 10 is constructed with interior threads 11 for engaging upper exterior threads 12 on insert member 3 whereby the complete delivery system can be closed. The wick 4 comprises an interior core 13 of absorbent material and a protective tubular sheath 14 of plastic material. The top and bottom of the wick are open and are not covered by the sheath 14. The outer dimensions of the wick are such that it is frictionally engaged in the neck portion 15 of the insert member 3 and is thereby moved vertically as the insert member is rotated.

In a typical operation of the system, a dilute aqueous solution of sodium chlorite in the container 1 from which the closure member 10 has been removed moves upwardly by capillary action through the absorbent capillary material 13 in wick 4. The aqueous solution contacts the pad 9 which contains a molar excess of a reactive material, preferably a dry solid acid, e.g. sulfamic acid. The contact will be at the approximate center point of the pad 9. From the moment of contact, the sodium chlorite dissolved in the water will react with the acid to produce and evolve chlorine dioxide. As the acid at the center point is fully reacted and more aqueous sodium chlorite reaches the pad 9 from the wick 4, the reaction zone will expand radially outward from the center producing more chlorine dioxide until the reaction zone reaches the periphery of the pad 9 and the reaction stops. The water in the aqueous solution which reaches the pad evaporates concurrently with the evolution of the chlorine dioxide and assists in distributing the oxidizing agent throughout the area to be treated.

The container, insert member and closure member employed in the invention can be fabricated by standard techniques using any of a number of suitable polymers including, for example polyethylene, polypropylene, and polyethylene terephthalate. A suitable capacity for the container is 3-4 fluid ounces.

Suitable materials for the absorbent core of the wick include natural and synthetic fibers that are capable of being formed into a capillary wick. These include, for example, Scrimrod R manufactured by Baumgartner Papers S.A. The outer sheath 14 can be any wet-strength polymer capable of retaining the inner fibers. It may be permeable or nonpermeable. In the presently preferred embodiment, the absorbent fibers are polyester and the outer sheath is a polyester film.

The emanator pad may be made from woven or nonwoven materials capable of transporting liquids by capillary action, and preferably is a mixture of cotton, synthetic and wood pulp fibers, plus a wet strength binder.

The reactive material is preferably a non-volatile acid, preferably a dry solid acid such as sulfamic or citric acid. Other non-volitile acids which may be employed include hydrocarbon carboxylic acids of relatively high molecular weight such as lauric or dodecanoic acids or aromatic acids e.g. benzoic acid. The term "reactive material" as used herein, means any compound which will react with the sodium chlorite to produce chlorine dioxide such as aldehydes and amines. Reducing sugars such as glucose and fructose are useful.

It will be apparent from the foregoing discussion that the process of the embodiment of FIGS. 1 and 2 of this invention is a deodorizing process in which an aqueous solution of sodium chlorite in a closed container is transported through a wick by capillary action to contact a reactant preferably a dry acid in an absorbent emanator pad to react therewith and continuously produce and evolve from the pad controlled quantities of chlorine dioxide.

A particular advantage of the invention is that the system can be "turned off" whenever it is desired to do so. This is a significant economic advantage since the system can be operated only when there is a need to do so.

One method of turning off the system illustrated in FIGS. 1 and 2 is to remove the wick 4 from the reservoir 2 by rotating the insert 3. Another method is simply to close the system by replacing the closure member 10. With the closure member in place, the formation and evolution of chlorine dioxide ceases because of the increased pressure of the chlorine dioxide and water vapor is the space between the pad 9 and the closure member 10. This increased pressure reverses the chemical reaction which is an equilibrium reaction and also reverses the capillary movement in the wick 4 so that the movement of additional aqueous sodium chlorite through the wick ceases.

Figure 3:
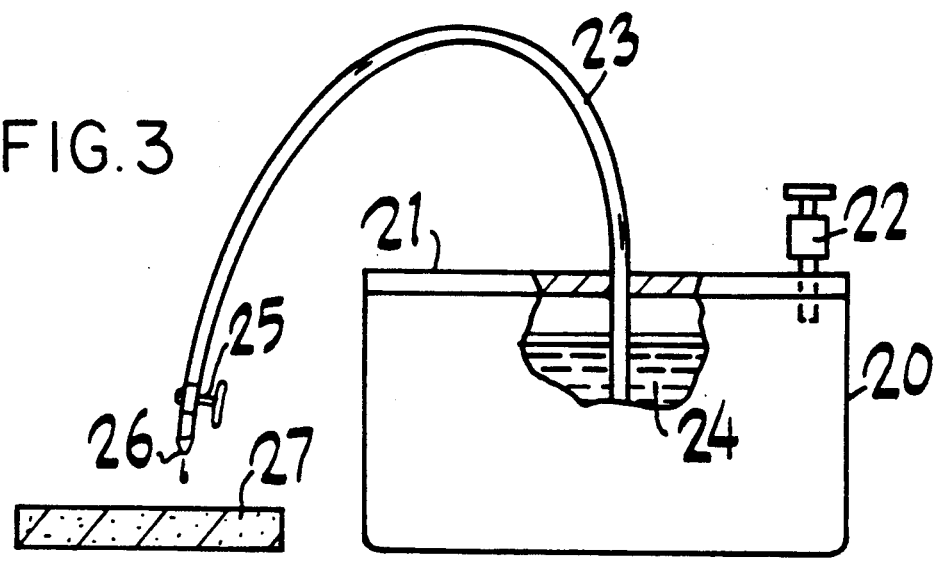
FIG. 3 is a side view, partly in cross-section, of the second embodiment of such devices.

In the embodiment illustrated in FIG. 3 the container 20 has an air-tight cover 21 and a finger-operated air pump 22. A thin tube 23 extends through cover 21 and into the sodium chlorite liquid 24 in container 20. The tube, at its opposite end, has a valve 25 and an exit orifice 26. The emanator pad 27 is positioned beneath the orifice 26 so that it receives drops from the tube 23. In operation, the user will raise the air pressure in container 20 by pumping the air pump 22. He will then open the valve 25 permitting the dilute aqueous solution of sodium chlorite to drip slowly on the pad 27, which contains a molar excess of a solid and, as described above in connection with pad 9. The system of FIG. 3 is shut off by closing the valve 25.

Figure 4:
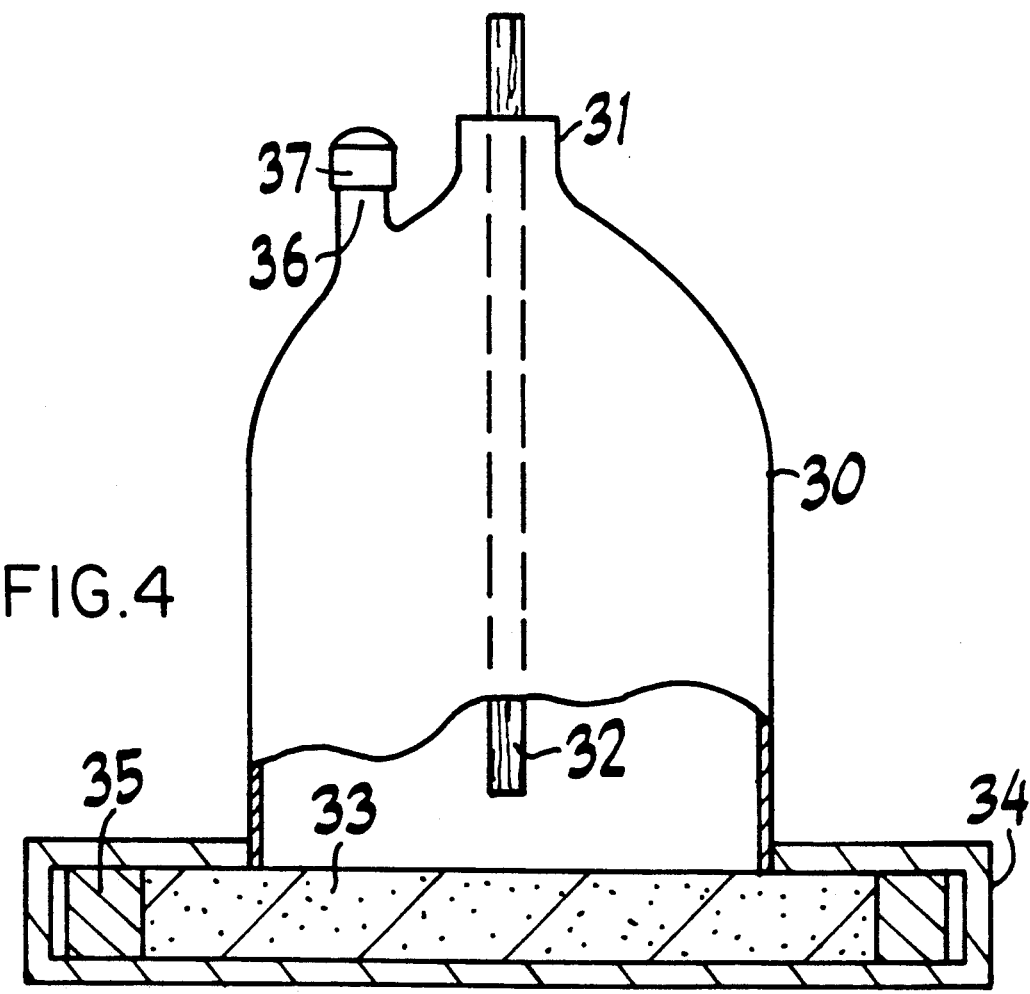
FIG. 4 is a cross-sectional view of the third embodiment of such devices.

In the embodiment illustrated in FIG. 4 the container 30 has an open neck portion 31 through which a capillary wick 32 extends. The emanator pad 33 is positioned below the wick 32 and held in pad container 34. The pad is absorbent and has a capillary action. The solid acid is located in a ring 35 near the outer edge of the pad. The wick 32 is filled with a dilute aqueous solution of sodium chlorite in liquid or gel form before the system of FIG. 4 is shipped from the factory. In operation the user lowers the wick 32 until it touches the pad 33. The sodium chlorite solution will be absorbed into the pad 33, reach the ring 35 of solid acid and chlorine dioxide will be generated which will pass out of the container 30 through vent hole 36 which is opened by removal of cap 37. Generation of the gas is halted by lifting the wick 32 from the pad 33 and/or replacement of the cap 37. The removable closure cap 37 screws onto neck 31.

In the embodiment illustrated in FIG. 5 the container 40 contains the dilute aqueous solution of sodium chlorite 41 which is formed into a gel-like consistency by a thickening or gelling agent, for example carboxymethyl cellulose. The sodium chlorite passes into the wick 42 by osmotic pressure and passes up the wick 42 by capillary action and osmotic pressure until it reaches the emanator pad 43 containing the dry acid. This system is shut down by placing a closure cap 44, shown by dashed lines, over the pad and 43 the top of the container 40.

Figure 6B:
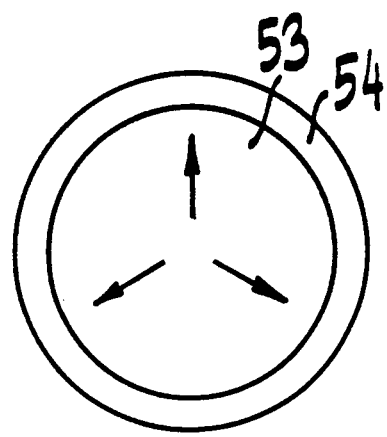
FIG. 6B is a top plan view of the pad used in the embodiment of FIG. 6A.

In the embodiment illustrated in FIGS. 6A, 6B the container 50 has an upper portion 51 containing the capillary wick 56 and a bottom portion 52 containing the emanator pad 53 having its dry acid in the form of a ring 54. The dilute aqueous solution 57 of sodium chlorite, in liquid or gel form, is held in the top tank 55, whose bottom orifice is closed by the wick 56. In operation the user removes the cap 58 thereby opening the vent hole 57 in the container 50. The sodium chlorite solution will travel down wick 56 to the center of the pad 53 and then outwardly, as shown by the arrows of FIG. 6B, to the ring 54 of dry acid. The generated gas is vented through vent hole 57. The reaction in this embodiment is halted by placing the cap 56 on the vent hole thereby closing the vent hole 56.

In the embodiment illustrated in FIG. 7 the container 60 having handle 68 contains the chlorite solution 61. A top cover 62 is hinged at hinge 63 so that its wick 64 may be lowered into the solution 61 (solid lines) or pivoted out of the solution (dash-dot lines).

The cover 62 contains an emanator pack 65, in contact with the wick 64 and having a solid, reactive material therein. A vent hole 66 having a removable cover 67 provides for the escape of the generated gas.

The essential reactants for the practice of this invention are the sodium chlorite and the selected reactive material. However, other components may be added to increase the efficiency of the process.

One such component is a buffer which will maintain the pH of the system above 9 thereby inhibiting spontaneous and unwanted production of chlorine dioxide. As is known, sodium chlorite in aqueous media initially has a pH of about 9. However, the chlorite tends to oxidize on standing to produce chlorine dioxide, and this increases the hydrogen ion concentration of the media, reduces the pH and increases the rate of chlorine dioxide production. The shelf life of the products of this invention can be increased by the utilization of a buffer selected to maintain the pH at 9 or above.

Many buffers are available which can be employed to maintain the desired pH. Of these, sodium bicarbonate is preferred. The reason that sodium bicarbonate is preferred is that it will react with the acid in the emanator pad to produce carbon dioxide. The carbon dioxide facilitates the release of chlorine dioxide from the pad because they are released together. If sodium bicarbonate or other carbon dioxide producing buffer is employed, the amount of acid in the pad should be sufficiently high to insure complete reaction of both the buffer and the sodium chlorite.

The addition of volatile alcohols which are miscible with the aqueous sodium chlorite solution will increase the evaporation rate of the chlorine dioxide and water from the pad as well as the evolution rate of the carbon dioxide if a buffer which produces this product is employed. Any water soluble alkanol containing up to about four carbon atoms can be used for this purpose. Isopropyl alcohol is preferred.

The use of surfactants in the aqueous sodium chlorite solution will assist in wetting the liquid onto the wick and the pad thereby improving the rate of capillary movement, the rate of reaction and the rate of evolution. Any of a wide variety of nonionic and anionic surfactants can be employed for this purpose. The presently preferred surfactant is Triton X-100 R which is an ethoxylated nonyl phenol.

The presently preferred acid for use on the emanator pad is sulfamic acid, preferably employed in association with sodium bisulfate which is also an acid. Other organic and inorganic acids including, for example, citric acid may also be employed.

To assist in uniform distribution of the acid throughout the pad, it is preferred that it be water soluble solid acid such as sulfamic or citric acid. Such acids can be dissolved in water, soaked into the pad and the water evaporated to effect uniform distribution of the dry acid within the pad.

For the production of controlled quantities of chlorine dioxide in accordance with the process of this invention, it is necessary to employ selected amounts of the reactants. The chlorite composition is transported to the pad in a "sequence of drops", for example the amount of liquid equal to such a sequence of drops transported by capillary action or about 20-100 drops per minute delivered from a pump device. The following table shows suitable ranges for each component in the chlorite composition as well as the preferred and most preferred ranges. All percents are by weight based on the total weight. The absorbent emanator pad will contain a molar excess of the selected reactant.

TABLE 1

|  | Range, wt % | Preferred, wt % | Most Preferred, wt % |
| --- | --- | --- | --- |
| NaClO$_2$ | 0.1-10 | 0.5-5 | 1-2 |
| Alcohol | 0-15 | 2-10 | 5-6 |
| Surfactant | 0-3 | 1-2 | 1-1.5 |
| Na$_2$CO$_3$ | 0-10 | 1-5 | 0.5-3 |
| Water | Q.S. | Q.S. | Q.S. |

The chlorine dioxide generating devices of this invention can be adapted to generate sufficient chlorine dioxide to act as either a deodorant or a germicide. The concentration ranges in Table 1 are applicable to either purpose. Generally speaking, the more concentrated solutions will be employed to produce germicidally effective amounts of chlorine dioxide and the more dilute solutions will be used to generate sufficient quantities of chlorine dioxide to be effective as a deodorant.

However, concentration is not the only parameter which can be used to control chlorine dioxide production. The rate of capillary movement of the solution from the container to the absorbent pad can also effect the rate of chlorine dioxide production. Thus, dilute solutions within the above ranges can be employed if the rate of movement from the container to the pad is relatively fast. The rate should be decreased with more concentrated solutions.

While some flexibility is possible, deodorantly effective concentrations of chlorine dioxide may range up to 0.01 ppm in a closed space. However, it is generally preferred to maintain the concentration no higher than 0.005 ppm, say about, 0.002 to 0.004 ppm Germicidally effective concentrations are conveniently et at about 1 ppm to 50 ppm, although appreciably higher concentrations may be employed. Of course the area should be evacuated during the germicidal treatment.

I claim:

1. A method for the generation of controlled quantities of chlorine dioxide, including the step of:

selectively transporting an aqueous solution by the capillary action of a wick from a container reservoir containing from about 0.1% to 10% sodium chlorite by weight to contact at a controlled sequence of drops rate with an absorbent pad positioned adjacent the container, the pad having therein a non-volatile reactive material that reacts with the solution to generate chlorine dioxide gas.

2. The method of claim 1 and including the steps of controlling the reaction by opening and closing a closure of a vent hole of the container.

3. The method of claim 1 and including the steps of controlling the reaction by manually bringing the wick into contact with the pad to commence the reaction and manually removing the wick from the pad to halt the reaction.

4. The method of claim 1 wherein the solution is in a wick and the wick is selectively brought into contact with the pad to start the reaction and then removed from the pad to halt the reaction 5. The method of claim 1 wherein the reactive material is a dry acid before it is wetted by the solution.

* * * * *